United States Patent [19]

Falk

[11] 4,116,070
[45] Sep. 26, 1978

[54] MOLTEN METAL SAMPLER WITH REFRACTORY MOLD HALVES

[76] Inventor: Richard A. Falk, 519 Westminster Dr., Waukesha, Wis. 53186

[21] Appl. No.: 825,800

[22] Filed: Aug. 18, 1977

[51] Int. Cl.² ............................................... G01N 1/12
[52] U.S. Cl. ............................................... 73/425.4 R
[58] Field of Search ..................... 73/425.4 R, DIG. 9

[56] References Cited

U.S. PATENT DOCUMENTS

| 3,552,214 | 1/1971 | Collins | 73/DIG. 9 |
| 3,877,309 | 4/1975 | Hance | 73/DIG. 9 |
| 4,007,640 | 2/1977 | Boron | 73/DIG. 9 |
| 4,046,016 | 9/1977 | Hackett | 73/425.4 R |

Primary Examiner—S. Clement Swisher

Attorney, Agent, or Firm—Wheeler, Morsell, House & Fuller

[57] ABSTRACT

A molten metal sampler includes a three-part refractory sample cartridge carried in a paperboard sleeve. The cartridge includes an open ended refractory mixing chamber which in one embodiment has a side entry port which receives molten metal from a side port in the paperboard sleeve. The cartridge also includes two refractory mold halves having opposed recesses which define a fill passage and a sample forming cavity. The fill passage is positioned to receive molten metal from the open end of the entry chamber. In another embodiment, the mixing chamber has an inlet in the end of the chamber and an outlet to adapt the cartridge for use in an end filling sampler.

3 Claims, 8 Drawing Figures

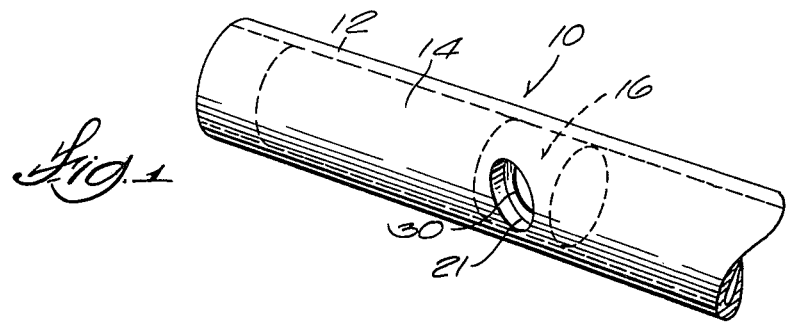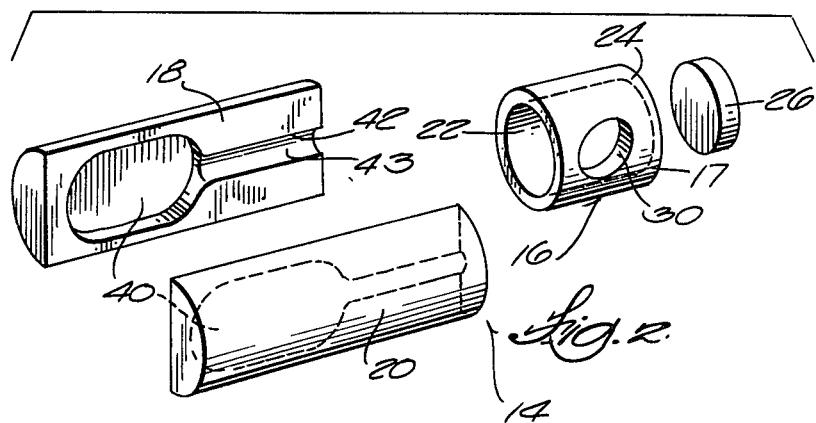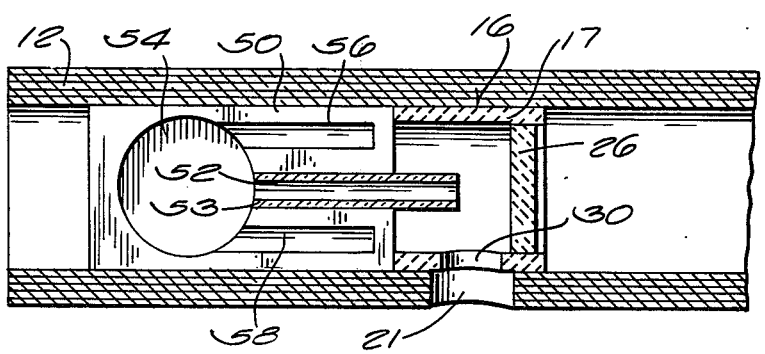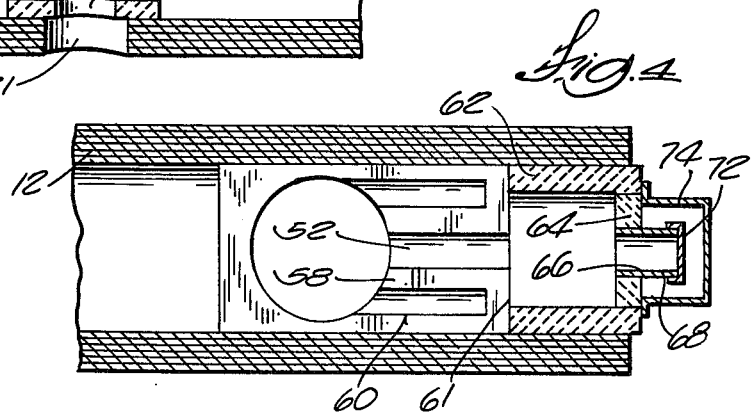

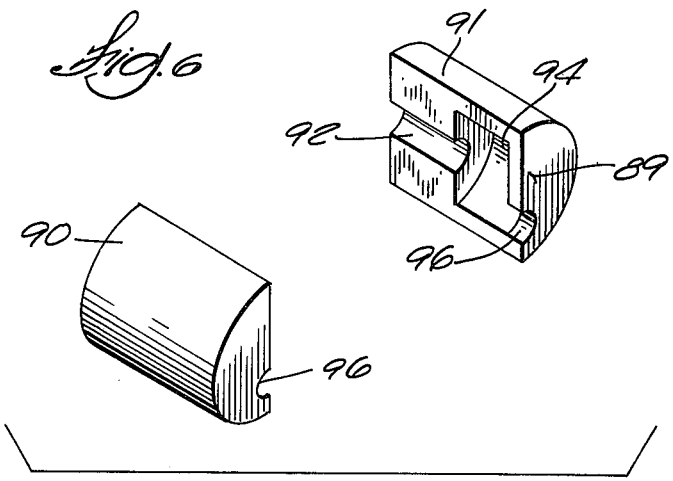
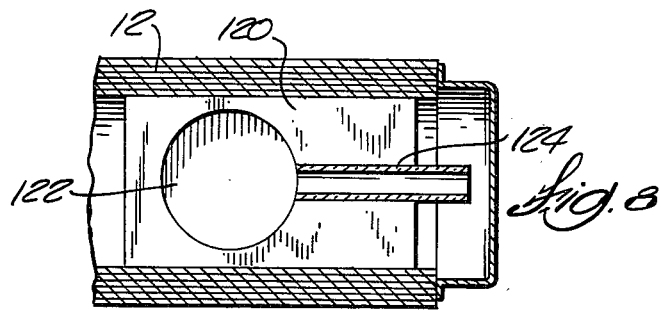
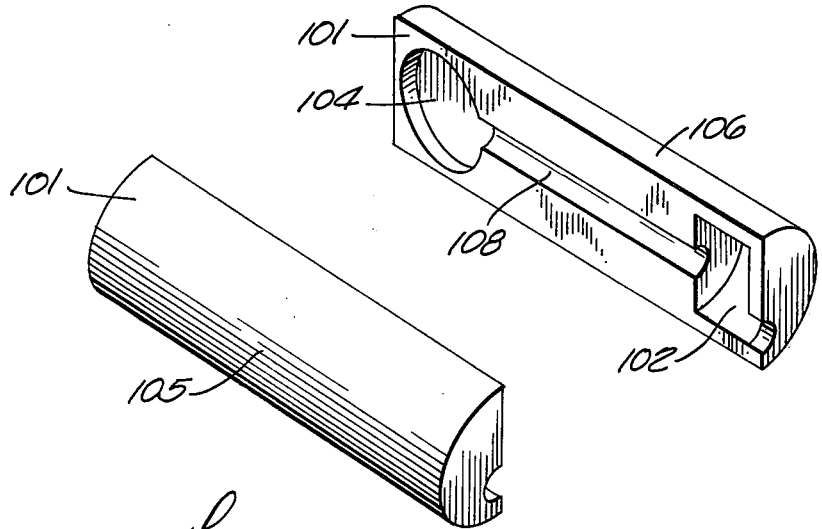

MOLTEN METAL SAMPLER WITH REFRACTORY MOLD HALVES

BACKGROUND OF INVENTION

The invention relates to molten metal sampling devices and in particular to a sample cartridge formed from two refractory mold halves. In my prior U.S. Pat. No. 3,481,201, I disclose a refractory cartridge in the form of a cylinder which has a side entry port for receiving molten metal. The sample shapes that can be formed with the cartridges disclosed in this patent are limited and may not be an appropriate size and shape for analysis without any machining operations. Moreover, the mold parts are usable only for immersion sampling with a cartridge having a side entry port and are not adapted for use in stream sampling or pneumatic sampling. The metal mold parts are not usable in extremely high temperature sampling and do not readily fill with molten metal in immersion sampling where the melt is at a low temperature of around 2500° F.

My prior U.S. Pat. No. 3,791,219 discloses an immersion sampler which forms both a disc shaped sample and a pin sample at the same time. However, the disc shaped sample cavity is formed by opposed metal mold halves rather than refractory mold parts. The present invention provides refractory mold halves which can be formed with recesses of any suitable shape to provide samples ready for immediate analysis.

SUMMARY OF INVENTION

The invention provides a molten metal sampling cartridge with refractory mold halves which can be used in either an end fill lance or a lance with a side entry port when employed with a refractory mixing chamber. The refractory mixing chamber is cylindrical in shape to snugly interfit in a paperboard sleeve and has an open end to supply molten metal to the mold halves and in one embodiment a side entry port for receiving metal from the side entry port in the cardboard sleeve or lance. The sample mold is in the form of two halves of a cylinder split longitudinally and in a diametral plane. Recesses in the mold parts remote from the fill end of the mold halves can be disc shaped to form a disc sample suitable for spectrographic analysis. Recesses communicating with the disc shaped cavity for receiving molten metal therefrom form pin samples suitable for combustion analysis. One or more sets of pin sample recesses can be employed.

When using the mold halves in an end fill lance, the refractory mixing chamber has an axial inlet and outlet. The end fill sampler can be used for stream sampling and immersion sampling and can be used with a vacuum pump.

With the end fill embodiment, tests have shown the sampling apparatus particularly suited for cool melts such as 2500° F. with good entry of metal into the sampler. In my prior art samplers, such as that shown in U.S. Pat. No. 3,791,219, very little metal flow into the sample cavity occurs when the molten metal source is around 2500° F. The reason for success of the sampler of the invention with cool molten metal melts is not presently understood.

The versatility of the mold parts disclosed herein for a wide range of samplers reduces manufacturing costs and thus the costs of the user.

Further objects, advantages and features of the invention will become apparent from the disclosure.

DESCRIPTION OF THE DRAWINGS

FIG. 1 is a perspective view of a sampling apparatus in accordance with the invention.

FIG. 2 is an exploded perspective view of a sample cartridge in accordance with the invention.

FIG. 3 is a sectional view of a sampler with pin forming recesses.

FIG. 4 is a sectional view of an end fill sampler in accordance with the invention.

FIG. 5 is a perspective view of a sample formed by the molds shown in FIGS. 3 and 4.

FIG. 6 is a perspective view of parts of a modified form of mixing chamber.

FIG. 7 is a perspective view of a modified embodiment with mold halves incorporating recesses for a mixing chamber.

FIG. 8 is a sectional view of a further modified embodiment of an immersion sampler.

PREFERRED EMBODIMENT OF INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The sampling apparatus 10 includes a thick walled paperboard sleeve 12 and includes a sample cartridge 14 which includes two mold halves 18 and 20 (FIGS. 1, 2). When the mold halves 18 and 20 are used in a lance which has a side entry port 21, a mixing chamber 16 is employed. The mixing chamber 16 has a refractory cylindrical wall 17 having an open end 22 and an end 24 sealed with a plug 26 which can be sealed to the wall 17 by refractory cement. The mixing chamber 16 also includes a side entry port 30 which is positioned in registry with the fill port 21 in the side of the paperboard sleeve 12 when the cartridge parts are assembled in the sleeve 12. The mold halves 18 and 20 can be provided with recesses to form samples of any shape desired. As illustrated in FIG. 2, the mold halves 18 and 20 are half sections of a refractory cylinder split along a longitudinal and diametral plane and have oblong recesses 40 and elongated recesses 42 which together form a fill passage 43. When the mixing chamber 16 and mold halves 18 and 20 are positioned in the sleeve 12, the fill passage 43 is positioned adjacent the open end 22 of the entry chamber 16 to receive molten metal from the mixing chamber 16 which can include a quantity of deoxidant.

FIG. 3 shows a mold half 50 which includes a recess 52 which communicates with a disc shaped cavity 54 which together with the other mold half, now shown in FIG. 3, form a disc shaped sample. Recesses 56 and 58 communicate with the cavity 54 to receive metal therefrom and cooperate with the oppositely located mold half (not shown) to form pin samples. A fused quartz fill tube 53 is desirably employed.

FIG. 4 illustrates a mold half 60 positioned so that the fill recesses 52 are in registry with the outlet 61 of a cylindrical mixing chamber 62. The mixing chamber 62 has an end wall 64 with an inlet 66 which can be provided with a fill tube 68 provided with a fusible cap 72 and a protective cover 74. The fused quartz tube 68 can have a beveled tip such as shown in my U.S. Pat. No. 3,859,857 for obtaining a stream sampler. The paperboard sleeve also can be short in length and used with pneumatic apparatus as shown in my U.S. Pat. No. 3,905,238.

FIG. 5 shows a sample 80 formed by the molds shown in FIGS. 3 and 4.

A modified embodiment of a mixing chamber 89 is illustrated in FIG. 6 and formed from two semi-cylindrical half sections 90, 91. Each half section includes an outlet recess 92, a mixing chamber recess 94 and a fill recess 96 which is offset from the outlet recess 92. The refractory mixing chamber 89 is adapted for use in an end fill lance as shown in FIG. 4. The offset inlet and outlet passages provide a tortuous path believed to enhance mixing of the molten metal with deoxidant contained in the mixing chamber.

FIG. 7 shows a further modified embodiment of an end fill sampler 101 in which the mixing chamber recesses 102 and sample forming recesses 104 are in the mold half sections 105, 106 and connected by fill recesses 108.

In FIG. 8, refractory half sections 120 are provided with sample forming recesses 122 and a fill tube recess 124. A fused quartz fill tube extends beyond the end of the tube 12 and supplies molten metal to the recesses 122.

What I claim is:

1. Molten metal sampling apparatus comprising a sleeve, a side entry port in said sleeve, and a sample cartridge including refractory wall means defining a cylindrical mixing chamber having an open end and an entry port in the side wall in registry with said sleeve entry port to receive molten metal entering said side entry port, said sample cartridge including refractory mold halves having recesses, said mold halves cooperating to form a fill chamber and a sample forming cavity, with said fill passage being positioned in said sleeve in communication with said open end of said mixing chamber to receive metal therefrom.

2. Sampling apparatus in accordance with claim 1 wherein said mold halves include recesses to form a disc sample, with said fill passage communicating with said disc recess and including recesses extending from said disc recess and communicating therewith to receive metal therefrom to form a pin sample.

3. A molten metal sampler including a sleeve having an opening, wall means defining a cylindrical refractory mixing chamber in said sleeve, said mixing chamber having a fill passage and an outlet passage with said fill passage being positioned at said sleeve opening to receive molten metal when immersed in a melt, and refractory mold halves having recesses cooperating to define a fill passage, said mold halves being position in said sleeve to receive molten metal from said mixing chamber, and wherein said sleeve opening is in the side of said sleeve and said mixing chamber fill passage is in the side wall of said mixing chamber.

* * * * *